United States Patent
McDonald et al.

(10) Patent No.: US 9,775,882 B2
(45) Date of Patent: Oct. 3, 2017

(54) MEDICAL DEVICES AND METHODS INCLUDING POLYMERS HAVING BIOLOGICALLY ACTIVE AGENTS THEREIN

(75) Inventors: Phillip Edward McDonald, Plymouth, MN (US); Christopher M. Hobot, Tonka Bay, MN (US)

(73) Assignee: Medtronic, Inc., Minneapolis, MN (US)

( * ) Notice: Subject to any disclaimer, the term of this patent is extended or adjusted under 35 U.S.C. 154(b) by 871 days.

(21) Appl. No.: 12/234,011

(22) Filed: Sep. 19, 2008

(65) Prior Publication Data

US 2009/0081273 A1    Mar. 26, 2009

Related U.S. Application Data

(60) Provisional application No. 60/973,787, filed on Sep. 20, 2007.

(51) Int. Cl.
*A61K 38/18* (2006.01)
*A61L 27/34* (2006.01)
*A61L 27/54* (2006.01)

(52) U.S. Cl.
CPC .......... *A61K 38/1875* (2013.01); *A61L 27/34* (2013.01); *A61L 27/54* (2013.01); *A61L 2300/252* (2013.01); *A61L 2300/45* (2013.01); *A61L 2300/602* (2013.01)

(58) Field of Classification Search
None
See application file for complete search history.

(56) References Cited

U.S. PATENT DOCUMENTS

| | | | |
|---|---|---|---|
| 4,201,211 A * | 5/1980 | Chandrasekaran | A61K 9/7053 424/448 |
| 5,492,697 A * | 2/1996 | Boyan et al. | 623/16.11 |
| 5,837,313 A * | 11/1998 | Ding et al. | 427/2.21 |
| 6,008,431 A | 12/1999 | Caldarise et al. | |
| 6,013,853 A | 1/2000 | Athanasiou et al. | |
| 6,335,029 B1 | 1/2002 | Kamath et al. | |
| 6,528,097 B1 * | 3/2003 | Vaughn et al. | 424/501 |
| 2002/0102307 A1 | 8/2002 | Guo et al. | |
| 2002/0106393 A1 | 8/2002 | Bianchi et al. | |
| 2002/0110591 A1 | 8/2002 | Brubaker et al. | |
| 2002/0110635 A1 | 8/2002 | Brubaker et al. | |
| 2003/0118649 A1 | 6/2003 | Gao et al. | |
| 2004/0143221 A1 | 7/2004 | Shadduck | |
| 2004/0180075 A1 | 9/2004 | Robinson et al. | |
| 2004/0230303 A1 | 11/2004 | Gomes et al. | |
| 2004/0249471 A1 | 12/2004 | Bindseil et al. | |
| 2005/0008673 A1 | 1/2005 | Snyder et al. | |
| 2005/0017394 A1 | 1/2005 | Hochsmann et al. | |
| 2005/0037078 A1 * | 2/2005 | Kuo et al. | 424/469 |
| 2005/0244461 A1 * | 11/2005 | Nivaggioli et al. | 424/427 |
| 2005/0260247 A1 * | 11/2005 | Ralph et al. | 424/423 |
| 2006/0045902 A1 | 3/2006 | Serbousek | |

FOREIGN PATENT DOCUMENTS

| WO | WO 96/05038 | 2/1996 |
| WO | WO 2004/110308 A2 | 12/2004 |
| WO | WO 2005/034998 * | 4/2005 |

OTHER PUBLICATIONS

Filos, Kriton S., et al., Anesthesiology, V 81, No. 3, Sep. 1994, pp. 591-601.*
Finkelstein, Ariel, et al., Circulation, 2003, 107, pp. 777-784.*
Yang, Shoufeng, et al., Tissue Engineering, vol. 7, No. 6 (2001) pp. 679-689.*
Schulteis, Gery, Neuropsychopharmacology, (1998) 19:406-416.*
Kleinschmidt, et al., A multiphase system bone implant for regenerating the calvaria, Plastic and Reconstructive Surgery, 91(4):581-588, 1993.

* cited by examiner

*Primary Examiner* — Dennis J Parad
*Assistant Examiner* — Lyndsey Beckhardt

(57) ABSTRACT

Medical devices and methods including polymers having biologically active agents therein are disclosed. The medical devices can be useful as implantable devices such as orthopedic implants.

11 Claims, 4 Drawing Sheets

MEDICAL DEVICES AND METHODS INCLUDING POLYMERS HAVING BIOLOGICALLY ACTIVE AGENTS THEREIN

This application claims priority to U.S. Provisional Patent Application Ser. No. 60/973,787, filed on Sep. 20, 2007, which is hereby incorporated by reference in its entirety.

BACKGROUND

Medical devices that can deliver biologically active agents such as drugs to a tissue are finding use in a wide variety of applications. For example, implantable medical devices (i.e., implants) that are capable of delivering drugs to an adjacent tissue can be designed to offer advantageous performance ranging from treatment of diseases to prevention of adverse reactions and/or rejection of the implant by the body. Implantable medical devices are typically designed with a profile for releasing biologically active agents at a specified rate over a desired period of time.

For some applications it is desirable that an implantable medical device be capable of a nearly constant rate of release of biologically active agent (e.g., a therapeutic agent) over a sustained period of time (i.e., sustained release). Frequently such medical devices include a solvent-based coating that may optionally include the biologically active agent, with the coating being capable of modulating and/or controlling the release profile of the biologically active agent. However, application of such solvent-based coatings can be problematic, for example, in that the solvent may have an adverse effect on the medical device, particularly when the medical device includes polymeric material that can be softened or dissolved by the solvent. Further, the solvent can also have an adverse effect on the biologically active agent itself, particularly when the biologically active agent is a protein-based drug. Moreover, damage that may occur to a coated medical device while making or using the device can adversely affect the ultimate performance of the device.

There is a continuing need for new medical devices that are capable of releasing biologically active agents, and methods of making such devices.

SUMMARY

Medical devices that include a polymer having at least one biologically active agent therein are disclosed in the present application. In some embodiments, a medical device as disclosed herein does not include a coating having a biologically active agent disposed therein, and in certain embodiments, the medical device does not include any coatings thereon. In certain embodiments, the medical device is an implantable device (e.g., an orthopedic implant). Methods of using such medical devices to deliver a biologically active agent to a tissue are also disclosed herein.

In certain embodiments the medical device includes: a first section including a first polymer; a non-tubular second section attached to the first section, wherein the second section includes a second polymer having at least a first biologically active agent disposed therein; and a third section attached to the second section, wherein the third section includes a third polymer.

In additional embodiments, the medical device includes: a non-tubular first section including a first polymer; a non-tubular second section attached to the first section, wherein the second section is non-porous and includes a second polymer having at least one biologically active agent disposed therein.

In other certain embodiments, the medical device is a substantially cylindrically-shaped medical device that includes: a first disc including a first polymer; a second disc having a first face attached to a face of the first disc, wherein the second disc includes a second polymer having at least one biologically active agent disposed therein; and a third disc attached to a second face of the second disc, wherein the third disc includes a third polymer. In certain preferred embodiments, the substantially cylindrically-shaped medical device is solid. As used herein, the terms "disc" and "cylinder" are used interchangeably to refer to a cylindrically shaped object, i.e., an object having a shape generated by rotating a parallel line around a fixed line. In some embodiments, a disc or cylinder can have as aspect ratio (radius divided by height) of 1, less than 1 (e.g., 0.9, 0.7, 0.5, 0.3, 0.1, 0.01, or even smaller), or greater than 1 (e.g., 1.1, 1.5, 2, 3, 5, 10, 50, 100, or even greater). As used herein, cylindrically shaped objects are intended to encompass solid and/or hollow objects.

In some other embodiments, the medical device includes at least one section, wherein the at least one section includes a polymer having at least a first biologically active agent disposed therein; wherein the at least one section has a total surface area including an exposed surface area and a non-exposed surface area; and wherein the exposed surface area of the at least one section is at most 75% of the total surface area of the at least one section. As used herein, "exposed" surfaces are intended to refer to surfaces that are not covered by another material and that can be readily contacted by fluids such as air or bodily fluids. For porous surfaces, the "exposed" surface area can include the area of pores that are exposed (i.e., not covered by another material).

In even some other embodiments, the medical device includes at least one section, wherein the at least one section includes a polymer having at least a first biologically active agent disposed therein; wherein the at least one section has an exposed surface area and a non-exposed surface area; wherein the medical device has a total exposed surface area; and wherein the exposed surface area of the at least one section is at most 75% of the total exposed surface area of the medical device.

Methods of making the medical devices disclosed in the various embodiments disclosed herein are also provided. In certain embodiments the method includes: providing a first section of the medical device including a first polymer; attaching a non-tubular second section of the medical device to the first section, wherein the non-tubular second section includes a second polymer having at least one biologically active agent disposed therein; and attaching a third section of the medical device to the non-tubular second section, wherein the third section includes a third polymer. In some embodiments two or more sections of the medical device are attached to one another using heat and/or pressure, optionally with the two or more sections in a mold. In some other embodiments, two or more sections of the medical device are attached to one another using an adhesive and/or solvent.

In other certain embodiments, the method includes: providing a non-tubular first section of the medical device including a first polymer; and attaching a non-tubular second section of the medical device to the first section, wherein the non-tubular second section is non-porous and includes a second polymer having at least one biologically active agent disposed therein.

In other certain embodiments, the method includes: providing a first section having a total surface area and including a polymer having a biologically active agent disposed therein; and attaching one or more additional sections to at least 25% of the total surface area of the first section, thus forming a non-exposed surface area where the one or more additional sections are attached, and leaving an exposed surface area of the first section where no additional sections are attached.

In other certain embodiments, the method includes: providing a first section having a total surface area and including a polymer having a biologically active agent disposed therein; and attaching one or more additional sections to a portion of the total surface area of the first section, thus leaving an exposed surface area of the first section where no additional sections are attached, and forming a medical device having a total exposed surface area, wherein the exposed surface area of the first section is at most 75% of the total exposed surface area of the medical device.

In other certain embodiments, the method includes making a substantially cylindrically-shaped medical device. The method includes: providing a first disc including a first polymer; attaching a first face of a second disc to a face of the first disc, wherein the second disc includes a second polymer having at least one biologically active agent disposed therein; and attaching a third disc to a second face of the second disc, wherein the third disc includes a third polymer.

Methods of making at least a section of a medical device are also disclosed herein. In certain embodiments, the method includes: combining particles of a polymer and particles of at least one biologically active agent to form a mixture; and processing the mixture to provide a polymeric composite having the at least one biologically active agent disposed therein.

In certain embodiments, one or more medical devices as disclosed herein can be used for delivering a biologically active agent to a tissue. The method includes: placing one or more medical devices as disclosed herein proximate a tissue; and allowing the one or more medical devices to deliver at least one biologically active agent to the tissue.

Medical devices as disclosed herein can, in certain embodiments, be advantageously used for sustained release of biologically active agents such as protein-based drugs. In certain embodiments, the biologically active agent can be incorporated in a polymeric section of the device without using solvents. Methods that do not require solvents can be particularly advantageous when using biologically active agents that can be adversely effected by exposure to solvents (e.g., proteins), and the use of such methods can result, for example, in increased stability of the biologically active agent and improved release properties of the biologically active agent from the medical device.

Further, in certain embodiments, the biologically active agent can be incorporated in a polymeric section of the device at a high enough concentration to allow for uniform dispersion of the biologically active agent in the polymeric section, while preventing undesirably high release rates by controlling the exposed surface area of biologically active agent-containing section. Further, the release profile can be tuned, for example, by controlling the surface area of at least the portion of the medical device that can release the biologically active agent, and controlling the concentration of the biologically active agent in that portion of the device.

The term "comprises" and variations thereof do not have a limiting meaning where these terms appear in the description and claims.

As used herein, "a," "an," "the," "at least one," and "one or more" are used interchangeably.

As used herein, the term "or" is generally employed in the sense as including "and/or" unless the context of the usage clearly indicates otherwise.

Also herein, the recitations of numerical ranges by endpoints include all numbers subsumed within that range (e.g., 1 to 5 includes 1, 1.5, 2, 2.75, 3, 3.80, 4, 5, etc.).

The above summary is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
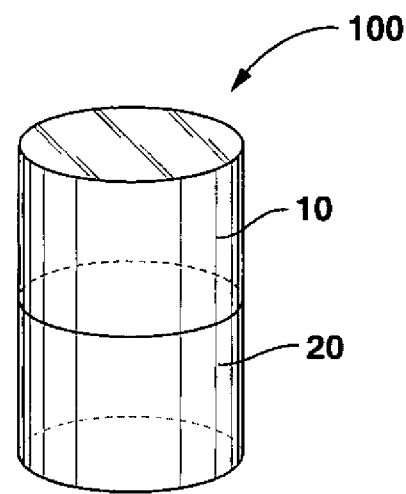
FIG. 1 is a perspective view of an embodiment of a medical device having two sections.

One embodiment of a medical device that includes a polymer having at least one biologically active agent therein is illustrated in FIG. 1. FIG. 1 illustrates an embodiment in which medical device 100 is disc or cylindrically shaped. However, it should be understood that medical device 100 can be any shape as desired (e.g., cube, rhomboid, cone, pyramid, sphere, ellipsoid, tetrahedron, polyhedron, other regular shapes, other irregular shapes, and the like), with the shape generally depending on the application for which the medical device is to be used. For example, cylinder shaped devices as illustrated in FIG. 1 can be used as orthopedic implants.

Medical device 100 includes first polymeric section 10 attached to second non-tubular polymeric section 20. As used herein, "non-tubular" means that the shape is not in the form of a tube, i.e., hollow or pipe-like. In contrast, a tubular shape would be formed, for example, by a coating on a cylindrically shaped article. As used herein, the term "polymeric section" means that the section includes a polymer, and preferably an organic polymer. As illustrated in FIG. 1, section 10 is disc shaped, although section 10 can be any shape as desired to form the final shape of the medical device.

Section 10 includes a first polymer. In the embodiment illustrated in FIG. 1, section 10 is also illustrated as being non-tubular, although in certain embodiments section 10 can be any shape as desired. The first polymer can be a thermoplastic polymer or a thermoset polymer. The first polymer can be crystalline, semicrystalline, or amorphous.

Section 10 can be porous or non-porous. As used herein, "porous" is used to refer to an object that has at least 50% void volume, preferably at least 55%, 60%, 65%, 70%, 75%, 80%, 85%, 90%, or even 95% or higher void volume. As used herein, "non-porous" is used to refer to an object that has less than 50% void volume, preferably at most 45%, 40%, 35%, 30%, 25%, 20%, 15%, 10%, 5%, or even 0% void volume. As used herein, "void volume" means unoccupied space, and percent void volume can be conveniently determined by dividing the density of the sample by the density of the fully-densified polymer.

The first polymer can be biostable or biodegradable. As used herein, "biodegradable" and "bioerodible" are used interchangeably and are intended to broadly encompass materials including, for example, those that tend to break down upon exposure to physiological environments. Biodegradable and/or bioerodible polymers known in the art include, for example, linear aliphatic polyester homopolymers (e.g., polyglycolide, polylactide, polycaprolactone, and polyhydroxybutyrate) and copolymers (e.g., poly(glycolide-co-lactide), poly(glycolide-co-caprolactone), poly(glycolide-co-trimethylenecarbonate), poly(lactic acid-co-lysine), poly(lactide-co-urethane), poly(ester-co-amide)); polyanhydrides; polyketals; and poly(orthoesters).

As illustrated in FIG. 1, section 20 is disc shaped, although section 20 can be any shape as desired to form the final shape of the medical device. Section 20 includes a second polymer having at least a first biologically active agent disposed therein. As used herein, the term "disposed" is intended to be broadly interpreted as inclusive of dispersed, dissolved, suspended, or otherwise contained at least partially therein or thereon. The second polymer can be a thermoplastic polymer or a thermoset polymer. The second polymer can be crystalline, semicrystalline, or amorphous. The second polymer can be biostable or biodegradable.

The second polymer can be the same as or different than the first polymer. In certain embodiments, the first polymer and the second polymer can differ by one or more characteristics selected from the group consisting of chemical structure, morphology, molecular weight, hydrophilicity, hydrophobicity, porosity, biodegradability, degradation rate, tacticity, toughness, and mechanical properties. Section 20 can be porous or non-porous.

Section 10 may optionally include at least a second biologically active agent disposed therein. The second biologically active agent can be the same as or different than the first biologically active agent, and the concentration of the second biologically active agent in section 10 can be the same as or different than the concentration of the first biologically active agent in section 20.

Medical device 100 can optionally include one or more additional sections not illustrated in FIG. 1. Optional additional sections can be polymeric or non-polymeric. Optional additional polymeric sections can in all respects be similar to or different from section 10 described herein with respect to FIG. 1.

Figure 2:
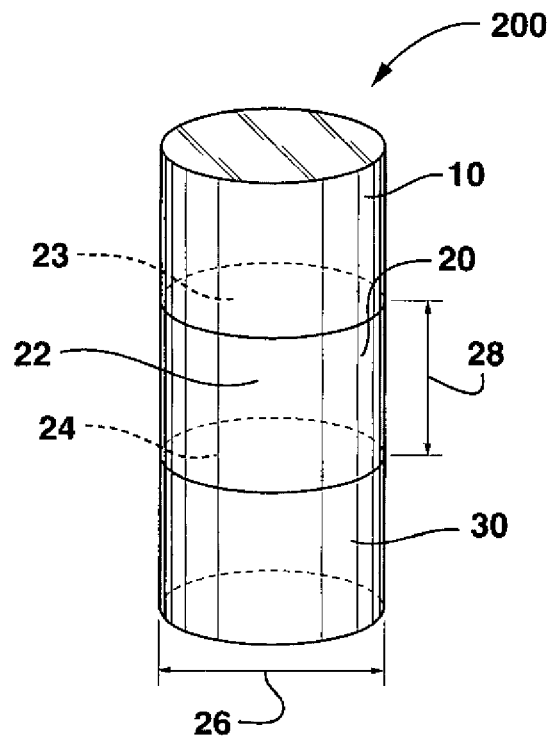
FIG. 2 is a perspective view of an embodiment of a medical device having three sections.

For example, another embodiment of a medical device that includes a polymer having at least one biologically active agent therein is illustrated in FIG. 2. Again, FIG. 2 illustrates an illustrative embodiment in which medical device 200 is cylindrically shaped. However, it should be understood that medical device 200 can be any shape as desired (e.g., cube, rhomboid, cone, pyramid, sphere, ellipsoid, tetrahedron, polyhedron, other regular shapes, other irregular shapes, and the like), with the shape generally depending on the application for which the medical device is to be used. For example, cylinder shaped devices as illustrated in FIG. 2 can be used, for example, as orthopedic implants.

Medical device 200 includes first polymeric section 10 attached to second non-tubular polymeric section 20. Sections 10 and 20 can be similar in all respects to sections 10 and 20 described herein with respect to FIG. 1. Additionally, medical device 200 includes third section 30 attached to section 20.

As illustrated in FIG. 2, section 30 is disc shaped, although section 30 can be any shape as desired to form the final shape of the medical device. Section 30 can include a third polymer. In the embodiment illustrated in FIG. 2, section 30 is also illustrated as being non-tubular, although in certain embodiments section 30 can be any shape as desired. Section 30 can be porous or non-porous. The third polymer can be a thermoplastic polymer or a thermoset polymer. The third polymer can be crystalline, semicrystalline, or amorphous. The third polymer can be biostable or biodegradable.

The third polymer can be the same as or different than the first and second polymers. In certain embodiments, the third polymer differs from the first and/or second polymers by one or more characteristics selected from the group consisting of chemical structure, morphology, molecular weight, hydrophilicity, hydrophobicity, porosity, biodegradability, degradation rate, tacticity, toughness, and mechanical properties.

Section 30 may optionally include at least a third biologically active agent disposed therein. The third biologically active agent can be the same as or different than the first and/or optional second biologically active agent(s), and the concentration of the third biologically active agent in section 30 can be the same as or different than the concentration of the first and/or optional second biologically active agent(s) in sections 20 and 10, respectively.

As illustrated in FIG. 2, section 20 includes exposed surface 22 and surfaces 23 and 24 that are attached to sections 10 and 30, respectively. Exposed surface 22 can be hydrophilic or hydrophobic. It should be recognized that the ratio of exposed surface 22 of section 20 to the total surface area of section 20 (i.e., the total area of surfaces 22, 23, and 24) can be controlled, for example, by varying the dimensions (e.g., diameter 26 and thickness 28) of section 20 as desired.

For some embodiments of medical devices as disclosed herein, the exposed surface area of a section including at least one biologically active agent disposed therein is at most 75%, 70%, 65%, 60%, 55%, 50%, 45%, 40%, 35%, 30%, 25%, 20%, 15%, 10%, or even 5% or less of the total surface area of the section. In preferred embodiments, the section including the at least one biologically active agent is a non-tubular section. Typically at least 50%, 60%, 70%, 80%, 90%, or even substantially all of the non-exposed surface area of the at least one section is in contact with one or more additional sections (e.g., polymeric sections) of the medical device.

For some other embodiments of medical devices as disclosed herein, the exposed surface area of a section including at least one biologically active agent disposed therein is at most 75%, 70%, 65%, 60%, 55%, 50%, 45%, 40%, 35%, 30%, 25%, 20%, 15%, 10%, or even 5% or less of the total exposed surface area of the medical device. In preferred embodiments, the section including the at least one biologically active agent is a non-tubular section. Typically at least 50%, 60%, 70%, 80%, 90%, or even substantially all of the non-exposed surface area of the at least one section is in contact with one or more additional sections (e.g., polymeric sections) of the medical device.

Biologically active agents can be disposed in section 20 of medical devices as illustrated in FIGS. 1 and 2 by a wide variety of methods. For example, section 20 can be formed by combining particles of a polymer and particles of at least one biologically active agent to form a mixture, and processing the mixture to provide a polymeric composite having the at least one biologically active agent disposed therein. Section 20 can thus be formed without the use of a solvent.

The polymer particles can be obtained by a wide variety of methods known to those skilled in the art. Preferably, the polymer can be ground by using liquid nitrogen to freeze the polymer and by using a mechanical milling apparatus to obtain particles of desired size. Other methods include, for example, precipitation of particles using a non-solvent for the polymer, spray drying, fluidized bed coating, hot melt precipitation, and/or other methods in which desired particle sizes can be achieved. In certain embodiments, the polymer particles have an average size of at least 10 micrometers, and preferably at least 60 micrometers. In certain embodiments, the polymer particles have an average size of at most 150 micrometers, and preferably at most 100 micrometers. As used herein, particle size refers to the diameter of spherical particles, and to the longest dimension for other shaped particles.

The at least one biologically active agent may be provided as particles or can be ground to provide particles of the at least one biologically active agent. The particles of the biologically active agent may be obtained by a wide variety of methods known to those skilled in the art. Specific methods include, for example, mechanical manipulation (e.g. mortar and pestle, dry milling), spray drying, lyophilization, solvent precipitation, hot melt precipitation, fluidized bed coating, and/or other methods in which a desired particle size can be achieved. In certain embodiments, the particles of biologically active agent have an average size of at least 1 micrometer, and preferably at least 5 micrometers. In certain embodiments, the particles of biologically active agent have an average size of at most 150 micrometers, and preferably at most 30 micrometers.

The particles of the polymer and the particles of the at least one biologically active agent can then be mixed. Preferred methods of mixing include those that do not require the use of a solvent, such as, for example, dry mixing (e.g., using a mortar and pestle). Wet mixing techniques can also be used providing that they result in a final dry mixture that is homogenous, that includes the desired particles size ranges, and that has acceptable residual solvent levels.

The mixture of particles of the polymer and the at least one biologically active agent can then be processed (e.g., fused) to provide section 20. The mixture can be processed by heating the mixture, pressurizing the mixture, or both. Optionally, the mixture can be processed by introducing the mixture into a mold, which can be heated, pressurized, or both. The mixture can be heated to a temperature sufficient to melt and/or fuse the particles together. A specific temperature that is sufficient to melt and/or fuse the particles together can be readily determined by one of skill in the art, and will commonly depend on, among other things, the characteristics of the polymer of the polymer particles including, for example, transition temperatures (e.g., glass transition temperature, $T_g$, and/or crystalline melt temperatures) and molecular weight of the polymer. For example, a temperature sufficient to melt and/or fuse the particles together can typically be 20° C. above the $T_g$ of the polymer. In a similar manner, polymer particles can be processed to provide other sections of the medical device that may or may not have biologically active agents disposed therein.

Alternatively, section 20 can be formed by methods known in the art. For example, the polymer and/or the biologically active agent can be dissolved, dispersed, or suspended in a solvent, followed by removal of the solvent to provide section 20.

Sections of medical devices as illustrated in FIGS. 1 and 2 can be attached to one another by a wide variety of methods. For example, polymeric sections may be attached to one another by application of heat and/or pressure, optionally in a mold. The polymeric sections can be heated to a temperature sufficient to melt and/or fuse the sections together. A specific temperature that is sufficient to melt and/or fuse the sections together can be readily determined by one of skill in the art, and will commonly depend on, among other things, the characteristics of the polymers of the polymeric sections including, for example, transition temperatures (e.g., glass transition temperature, $T_g$, and/or crystalline melt temperatures) and molecular weights of the polymers. For example, a temperature sufficient to melt and/or fuse the sections together can typically be 20° C. above the $T_g$ of at least one polymer of the polymeric sections.

Alternatively, or in addition to the melt/fusion methods described above, a solvent and/or an adhesive can be used to attach the sections to one another. A wide variety of solvents can be used including, for example, tetrahydrofuran (THF), ethanol, methanol, ethylacetate, dimethylformamide (DMF), dimethyacetamide (DMA), dimethylsulfoxide (DMSO), dioxane, N-methyl pyrollidone, chloroform, hexane, heptane, cyclohexane, toluene, formic acid, acetic acid, and/or dichloromethane.

Sections of medical devices as illustrated in FIGS. 1 and 2 can be attached to one another so as to form a medical device wherein the exposed surface area of a section including at least one biologically active agent disposed therein is at most 75%, 70%, 65%, 60%, 55%, 50%, 45%, 40%, 35%, 30%, 25%, 20%, 15%, 10%, or even 5% or less of the total surface area of the section. For example, one or more additional sections can be attached to a first section having a total surface area and comprising a polymer having a biologically active agent disposed therein. Specifically the one or more additional sections can be attached to at least 25%, 30%, 35%, 40%, 45%, 50%, 55%, 60%, 65%, 70%, 75%, 80%, 85%, 90%, or even 95% or more of the total surface area of the first section, thus forming a non-exposed surface area where the one or more additional sections are attached, and leaving an exposed surface area of the first section where no additional sections are attached. In preferred embodiments, the section including the at least one biologically active agent is a non-tubular section. Typically at least 50%, 60%, 70%, 80%, 90%, or even substantially all of the non-exposed surface area of the at least one section is in contact with one or more additional sections (e.g., polymeric sections) of the medical device.

Alternatively and/or additionally, sections of medical devices as illustrated in FIGS. 1 and 2 can be attached to one another so as to form a medical device wherein the exposed surface area of a section including at least one biologically active agent disposed therein is at most 75%, 70%, 65%, 60%, 55%, 50%, 45%, 40%, 35%, 30%, 25%, 20%, 15%, 10%, or even 5% or less of the total exposed surface area of the medical device. For example, one or more additional sections can be attached to a first section having a total surface area and comprising a polymer having a biologically active agent disposed therein, thus forming a nonexposed surface area where the one or more additional sections are attached, and leaving an exposed surface area of the first section where no additional sections are attached. In preferred embodiments, the section including the at least one biologically active agent is a non-tubular section. Typically at least 50%, 60%, 70%, 80%, 90%, or even substantially all of the non-exposed surface area of the at least one section is in contact with one or more additional sections (e.g., polymeric sections) of the medical device.

As used herein, a "biologically active agent" is intended to be broadly interpreted as any agent capable of eliciting a response in a biological system such as, for example, living cell(s), tissue(s), organ(s), and being(s). Biologically active agents can include natural and/or synthetic agents. Thus, a biologically active agent is intended to be inclusive of any substance intended for use in the diagnosis, cure, mitigation, treatment, or prevention of disease or in the enhancement of desirable physical or mental development and conditions in a subject. The term "subject" as used herein is taken to include humans, sheep, horses, cattle, pigs, dogs, cats, rats, mice, birds, reptiles, fish, insects, arachnids, protists (e.g., protozoa), and prokaryotic bacteria. Preferably, the subject is a human or other mammal.

A preferred class of biologically active agents includes drugs. As used herein, the term "drug" means any therapeutic agent. Suitable drugs include inorganic and organic drugs, without limitation, and include drugs that act on the peripheral nerves, adrenergic receptors, cholinergic receptors, nervous system, skeletal muscles, cardiovascular system, smooth muscles, blood circulatory system, synaptic sites, neuro-effector junctional sites, endocrine system, hormone systems, immunological system, reproductive system, skeletal system, autocoid systems, alimentary and excretory systems (including urological systems), histamine systems, and the like. Such conditions, as well as others, can be advantageously treated using compositions as disclosed herein.

Suitable drugs include, for example, polypeptides (which is used herein to encompass a polymer of L- or D-amino acids of any length including peptides, oligopeptides, proteins, enzymes, hormones, etc.), polynucleotides (which is used herein to encompass a polymer of nucleic acids of any length including oligonucleotides, single- and double-stranded DNA, single- and double-stranded RNA, DNA/RNA chimeras, etc.), saccharides (e.g., mono-, di-, poly-saccharides, and mucopolysaccharides), vitamins, viral agents, and other living material, radionuclides, and the like. Examples include antithrombogenic and anticoagulant agents such as heparin, coumadin, protamine, and hirudin; antimicrobial agents such as antibiotics; antineoplastic agents and antiproliferative agents such as etoposide, podophylotoxin; antiplatelet agents including aspirin and dipyridamole; antimitotics (cytotoxic agents) and antimetabolites such as methotrexate, colchicine, azathioprine, vincristine, vinblastine, fluorouracil, adriamycin, and mutamycinnucleic acids; antidiabetic such as rosiglitazone maleate; and anti-inflammatory agents. Anti-inflammatory agents for use in the present invention include glucocorticoids, their salts, and derivatives thereof, such as cortisol, cortisone, fludrocortisone, Prednisone, Prednisolone, 6α-methylprednisolone, triamcinolone, betamethasone, dexamethasone, beclomethasone, aclomethasone, amcinonide, clebethasol and clocortolone.

Preferred classes of drugs include, for example, Plasmid DNA, genes, antisense oligonucleotides and other antisense agents, peptides, proteins, protein analogs, siRNA, shRNA, miRNA, ribozymes, DNAzymes and other DNA based agents, viral and non-viral vectors, lyposomes, cells, stem cells, antineoplastic agents, antiproliferative agents, anti-thrombogenic agents, anticoagulant agents, antiplatelet agents, antibiotics, anti-inflammatory agents, antimitotic agents, immunosuppressants, growth factors, cytokines, hormones, and combinations thereof. Examples of preferred drugs are bone morphogenetic proteins (BMP) including, for example, recombinant human bone morphogenetic protein (rhBMP-2).

Suitable drugs can have a variety of uses including, but are not limited to, anticonvulsants, analgesics, antiparkinsons, antiinflammatories (e.g., ibuprofen, fenbufen, cortisone, and the like), calcium antagonists, anesthetics (e.g., benoxinate, benzocaine, procaine, and the like), antibiotics (e.g., ciprofloxacin, norfloxacin, clofoctol, and the like), antimalarials, antiparasitics, antihypertensives, antihistamines, antipyretics, alpha-adrenergic agonists, alpha-blockers, biocides, bactericides, bronchial dilators, beta-adrenergic blocking drugs, contraceptives, cardiovascular drugs, calcium channel inhibitors, depressants, diagnostics, diuretics, electrolytes, enzymes, hypnotics, hormones, hypoglycemics, hyperglycemics, muscle contractants, muscle relaxants, neoplastics, glycoproteins, nucleoproteins, lipoproteins, ophthalmics, psychic energizers, sedatives, steroids sympathomimetics, parasympathomimetics, tranquilizers, urinary tract drugs, vaccines, vaginal drugs, vitamins, collagen, hyaluronic acid, nonsteroidal anti-inflammatory drugs, angiotensin converting enzymes, polynucleotides, polypeptides, polysaccharides, and the like.

Certain preferred embodiments include a drug selected from the group consisting of indomethacin, sulindac, diclofenal, etodolac, meclofenate, mefenamic acid, nambu-netone, piroxicam, phenylgutazone, meloxicam, dexam-ethoasone, betamethasone, dipropionate, diflorsasone diacetate, clobetasol propionate, galobetasol propionate, amcinomide, beclomethasone dipropionate, fluocinomide, betamethasone valerate, triamcinolone acetonide, penicillamine, hydroxychloroquine, sulfasalazine, azathioprine, minocycline, cyclophosphamide, methotrexate, cyclosporine, leflunomide, etanercept, infliximab, ascomycin, beta-estradiol, rosiglitazone, troglitazone, pioglitazone, S-nitrosoglutathione, gliotoxin G, panepoxydone, cycloep-oxydon tepoxalin, curcumin, a proteasome inhibitor (e.g., bortezomib, dipeptide boronic acid, lactacystin, bisphosphonate, zolendronate, epoxomicin), antisense c-myc, celo-coxib, valdecoxib, and combinations thereof.

Certain preferred embodiments include a drug selected from the group consisting of podophyllotoxin, mycophenolic acid, teniposide, etoposide, trans-retinoic acids, 9-cis retinoic acid, 13-cis retinoic acid, rapamycin, a rapalog (e.g., Everolimus, ABT-578), camptothecin, irinotecan, topotecan, tacromilus, mithramycin, mitobronitol, thiotepa, treosulfan, estramusting, chlormethine, carmustine, lomustine, busultan, mephalan, chlorambucil, ifosfamide, cyclophosph-amide, doxorubicin, epirubicin, aclarubicin, daunorubicin, mitosanthrone, bleomycin, cepecitabine, cytarabine, fludarabine, cladribine, gemtabine, 5-fluorouracil, mercaptopurine, tioguanine, vinblastine, vincristine, vindesine, vinorelbine, amsacrine, bexarotene, crisantaspase, decarbasine, hydrosycarbamide, pentostatin, carboplatin, cisplatin, oxi-platin, procarbazine, paclitaxel, docetaxel, epothilone A, epothilone B, epothilone D, baxiliximab, daclizumab, interferon alpha, interferon beta, maytansine, and combinations thereof.

Certain preferred embodiments include a drug selected from the group consisting of salicylic acid, fenbufen, cortisone, ibuprofen, diflunisal, sulindac, difluprednate, prednisone, medrysone, acematacin, indomethacin, meloxicam, camptothecin, benoxinate, benzocaine, procaine, ciprofloxacin, norfloxacin, clofoctol, dexamethasone, fluocinolone, ketorolac, pentoxifylline, rapamycin, ABT-578, gabapentin, baclofen, sulfasalazine, bupivacaine, sulindac, clonidine, etanercept, pegsunercept, and combinations thereof.

Medical devices (e.g., implantable medical devices) can be prepared using a wide variety of polymers. Preferred polymers include, but are not limited to, polyurethanes (e.g., polyether urethanes, polyester urethanes, and polycaprolactone urethanes), polyureas, polyurethane-ureas, polyesters (e.g., polyethylene terephthalate), polycarbonates, poly (meth)acrylates, polysulfones, polyimides, polyamides, epoxies, polyacetals, polyketals, poly(orthoesters), vinyl polymers, polyanhydrides, polytriazoles, silicone rubber, natural rubber, rubber latex, synthetic rubbers, polyether-polyamide block copolymers, polyester-polyether copolymers, and combinations and/or copolymers thereof. Exemplary polyesters include, for example, linear aliphatic polyester homopolymers (e.g., polyglycolide, polylactide, polycaprolactone, and polyhydroxybutyrate) and copolymers (e.g., poly(glycolide-co-lactide), poly(glycolide-co-caprolactone), poly(glycolide-co-trimethylenecarbonate), poly(lactic acid-co-lysine), poly(lactide-co-urethane), poly(ester-co-amide)).

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials:

A poly(orthoester) (POE) polymer was prepared from 3,9-diethylidene-2,4,8,10-tetraoxaspiro[5,5]-undecane) (DETOSU) and 1,6-hexanediol (HD) in a manner similar to that described in U.S. Provisional Application No. 60/817,560, filed Jun. 29, 2006.

All glassware used during the preparation was pyro-cleaned, washed with soap, rinsed with DI water, 0.1M NaOH, DI water, isopropanol, acetone, and then placed in a 110° C. oven to dry. Unless otherwise noted, all solvents and reagents were or can be obtained from Sigma-Aldrich Corp., St. Louis, Mo.

The preparation of DETOSU has been previously described. See, for example, Heller et al. in *Macromolecular Syntheses*, C. G. Overberger, Ed., Vol. 11, pp. 23-35, Wiley, N.Y. (1992); and U.S. Pat. No. 4,513,143 (Ng et al.), U.S. Pat. No. 4,532,335 (Helwing), and U.S. Pat. No. 6,863,782 (Newsome et al.). DETOSU was recrystallized from hexanes containing triethylamine until it was at least 99% pure as determined by the method of Pogany et al., *J. of Chromatography*, 508:179-186 (1990). Distillation was used to remove traces of hexane and triethylamine still present in the DETOSU before storage. The diol (1,6-hexanediol) was freshly dried by rotary-evaporation at 80° C. and 20 torr for at least 7 hours.

The polymers were prepared in anhydrous tetrahydrofuran (THF) stabilized with butylated hydroxytoluene (BHT) in a nitrogen atmosphere glovebox, at a concentration 16.8% solids by weight. The batch size was based on 5 grams of DETOSU. The weights of the reactants were measured to 4 decimal places using a 5-place analytical balance in the glovebox. The overall molar ratio of DETOSU to diol was 1.020. A 1% by weight para-toluenesulfonic acid (PTSA) in THF polymerization agent solution was added at a ratio of 8.2 microliters polymerization agent solution per mL THF used to dissolve the reactants. The polymerization agent was added after the reactants had completely dissolved with magnetic stirring. The solution was stirred for at least 18 hours, at which point a fourier transform infrared (FTIR) scan was performed to confirm the absence of hydroxyl peaks above 3000 cm$^{-1}$ and ketene acetal peaks at 1703 cm$^{-1}$ indicating completion of the reaction. The polymer was precipitated from THF into anhydrous methanol (with a few drops triethylamine) inside a nitrogen glovebox, with vigorous stirring in a Waring blender. The polymer was redissolved in a minimal amount of anhydrous THF, and precipitated a second time. The polymer was then placed in a Mylar boat in a vacuum oven (full vacuum, 50° C.) to dry for at least eighteen hours. The raw materials were characterized by GPC and DSC. The resulting polymer had a weight average molecular weight (Mw) of approximately 50,000 Da.

Recombinant human bone morphogenetic protein (rhBMP-2) was obtained from Wyeth (Andover, Mass.) as a lyophilized cake containing 0.5% (w/v) sucrose, 2.5% (w/v) glycine, 5.0 mM L-glutamic acid, 5.0 mM sodium chloride, and 0.01% (w/v) non-ionic surfactant available under the trade designation Polysorbate 80, pH 4.5.

Preparation of Solid Protein Rod Implants (2-Step Process):

POE polymer was cryo-milled using an 80 micrometer sieve filter to obtain dry powder of uniform particle size. A mixture of 5 wt % rhBMP-2 cake and 95 wt % POE powder was prepared by mixing at room temperature with a mortar and pestle. The mixture was added to a stainless steel cylindrical mold with a diameter of 2 mm and length 0.5 mm. The filled molds were placed in a Carver heat press set at 70° C. and heated for 5-10 minutes. The sample was then pressed at 4 metric tons with the pressure being released once the pressure gauge subsided to 3.25 metric tons. The mold was taken out of the press and allowed to cool at room temperature conditions for 15 minutes. The samples were pushed out the mold to yield protein loaded polymer discs with a theoretical rhBMP-2 load of approximately 9 micrograms.

Blank polymer rods were fabricated in a similar fashion. Briefly, sieved polymer powder was loaded into a predilled mold having a diameter of 2 mm and a length of 16 mm. The mold was fabricated from an acetal resin engineering plastic available under the trade designation DELRIN from DuPont (Wilmington, Del.). The mold was placed in a heat press at 70° C. and preheated for 5-10 minutes. Next, gauge pins of similar diameter were placed in the polymer filled holes and pressed to compact the polymer into rods. The mold was then taken out of the heat press and allowed to cool at room temperature conditions for 15 minutes. The samples were pushed out of the mold and cut to desired rod lengths.

Layered protein loaded rods were made by placing the protein loaded disc between the blank polymer rods. The layered rod was placed in the DELRIN mold described above, preheated, and then pressed at 70° C. to fuse the layers together.

Evaluation of rhBMP-2 Release:

Release of BMP-2 was carried out in phosphate buffered saline (Hyclone 0.0067M) pH 7.4 with 1M sodium chloride and 0.01 wt % bovine serum albumin. Protein loaded rods (approximately 10 micrograms theoretical rhBMP-2 loaded) were placed in glass scintillation vials containing 1.5 mL of release medium and incubated at 37° C. under mild agitation. At pre-selected times, the buffer was removed for analysis and replaced with new medium. The protein content of the release samples were assayed using a basic sandwich ELISA on a monoclonal antibody pre-coated microplate. Detection was accomplished with an enzyme linked polyclonal antibody and substrate with the color intensity being quantitatively read at 450 nm. A kit available under the trade designation HUMAN/MOUSE/RAT BMP-2 QUANTIKINE ELISA KIT from R&D systems (Minneapolis, Minn.) was used for the assay.

Figure 3:
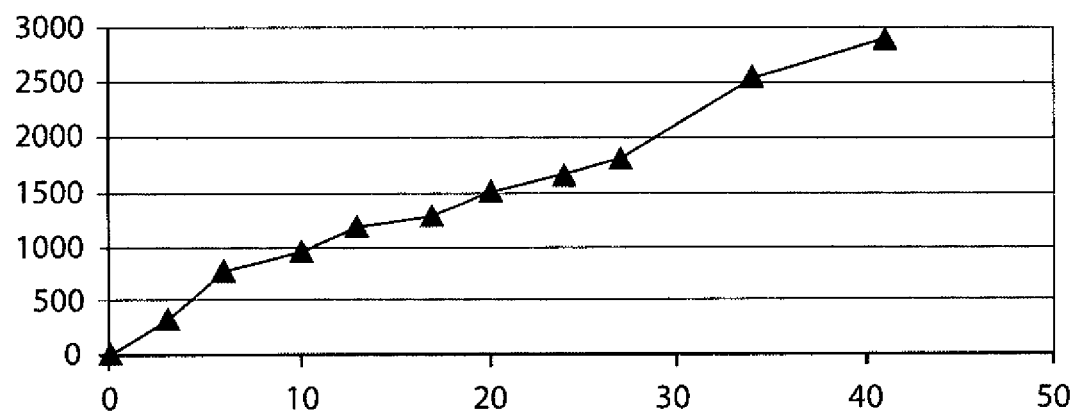
FIG. 3 is a graph illustrating the in vitro cumulative release of recombinant human bone morphogenetic protein (rhBMP-2) (y-axis; nanograms) over time (x-axis; days) from an implantable medical device prepared using a poly (orthoester) polymer as described in Example 1.

FIG. 3 is a graph showing the cumulative release of rhBMP-2 (nanograms) from the POE polymer over the given time period in days. The results demonstrate a smooth, controlled release of rhBMP-2 for 40 days. The rods released nanogram quantities of rhBMP-2 per day demonstrating the ability to release low amounts of active agent from a large volume implant.

Example 2

Materials:

The POE polymer was synthesized in a similar fashion as to that described in Example 1, except that 1,4-butanediol was used as the diol instead of 1,6-hexanediol.

Methods:

POE polymer was cryo-milled using an 80 micrometer sieve filter to obtain dry powder of uniform particle size. A mixture of 25 wt % rhBMP-2 cake and 75 wt % POE powder was prepared by mixing at room temperature with a mortar and pestle. The mixture was added to a DELRIN cylindrical mold with a diameter of 3 mm and length 12 mm. The filled molds were placed in a Carver heat press set at 70° C. and heated for 5-10 minutes. The sample was then pressed with gauge pins until resistance was indicated on the pressure sensor. The mold was taken out of the press and allowed to cool at room temperature conditions for 15 minutes. Then, milled POE polymer was back filled into the mold and compacted on top of the protein loaded rod already in the mold. The mold was once again preheated at 70° C. then pressed with gauge pins as before. The samples were cooled and pushed out the mold to yield protein loaded polymer rods with a blank polymer spacer. The rod was cut to an overall length of 5 mm by metering the protein loaded end to 2.5 mm and the blank polymer end to 2.5 mm. The theoretical rhBMP-2 load of the rod was approximately 450 micrograms.

For comparison, a drug loaded rod of equal total volume and having approximately the same theoretical loading of rhBMP-2 (450 micrograms) was prepared using a method similar to that described above except that the sample did not contain the blank polymer spacer, thus having rhBMP-2 distributed throughout the rod. The sample contained 10 wt % rhBMP-2 cake and 90 wt % POE powder. The rod had an overall length of 5 mm and a theoretical rhBMP-2 load of approximately 450 micrograms.

Evaluation of rhBMP-2 Release:

Release of rhBMP-2 was carried out in phosphate buffered saline (Hyclone 0.0067M) pH 7.4 with 1M sodium chloride. Protein loaded rods in triplicate (approximately 450 micrograms theoretical rhBMP-2 loading) were placed in glass scintillation vials containing 3 mL of release medium and incubated at 37° C. under mild agitation. At pre-selected times, the buffer was removed for analysis and replaced with new medium. The protein content of the release samples was assayed using a reverse phase high pressure liquid chromatograph (HPLC) method.

Figure 4:
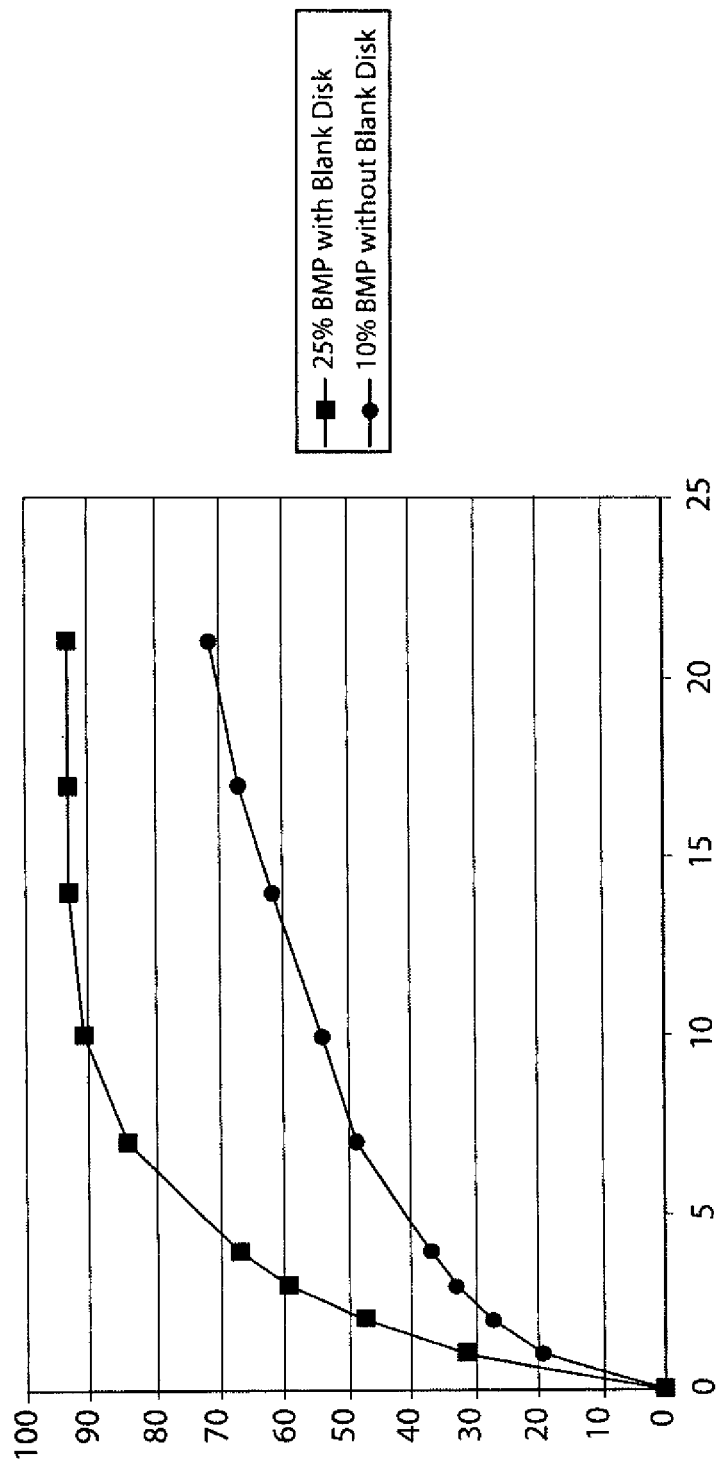
FIG. 4 is a graph illustrating the in vitro cumulative release of recombinant human bone morphogenetic protein (rhBMP-2) (y-axis; %) over time (x-axis; days) from an implantable medical device prepared using a poly(orthoester) polymer as described in Example 2.

FIG. 4 is a graph showing the cumulative release of rhBMP-2(%) from the POE polymer over the given time period in days. This example illustrates that the sample with the blank polymer spacer and having 25 wt % rhBMP-2 in the drug containing portion resulted in a higher elution rate compared with the sample without the blank polymer spacer that had equal total volume, 10 wt % rhBMP-2, and approximately the same loading of rhBMP-2 (450 micrograms).

Example 3

Materials:

Poly (lactide-co-glycolide) having an 50:50 lactide to glycolide ratio (PLGA 50:50), an intrinsic viscosity (IV) of 0.57 and ester end capped polymer chain ends was purchased from Lakeshore Biomaterials (Birmingham, Ala.). Also, PLGA 50:50 with an IV of 0.18 and acid end capped polymer chain ends was purchased from Lakeshore Biomaterials. Sulindac and clonidine HCl were purchased from Spectrum Chemicals (Gardena, Calif.).

Methods:

Both PLGA 50:50 polymers were cryo-milled using an 80 micrometer sieve filter to obtain dry powder of uniform particle size. A mixture of 30 wt % sulindac and 70 wt % PLGA 50:50 (IV=0.18) powder was prepared by mixing at room temperature with a mortar and pestle. The mixture was then added to a DELRIN cylindrical mold with a diameter of 3 mm and length 12 mm. The filled molds were placed in a Carver heat press set at 70° C. and heated for 5-10 minutes. The sample was then pressed with gauge pins until resistance was indicated on the pressure sensor. The mold was taken out of the press and allowed to cool at room temperature conditions for 15 minutes. The samples were cooled and pushed out the mold to yield sulindac loaded polymer rod with a theoretical loading of 1500 micrograms.

A sample containing 10 wt % clonidine HCl and 90 wt % PLGA 50:50 (IV=0.57) was prepared in a manner similar to that used for the sulindac sample described herein. The theoretical clonidine HCl loading was 3600 micrograms.

Next, a sulindac loaded rod and a clonidine HCl loaded rod were placed back into the mold. The mold was once again preheated at 70° C. then pressed with gauge pins as before. The samples were cooled and pushed out of the mold to yield a rod having two separate drug loaded sections. The sulindac portion of the rod was 0.5 mm in length and the clonidine HCl portion of the rod was 4.5 mm in length.

An additional sample was made using a method similar to those described above. However, the additional sample did not follow the layered polymer rod approach described herein above, but had sulindac and clonidine HCl distributed throughout the rod. The sample contained 3 wt % sulindac and 9 wt % clonidine. The rod had an overall length of 5 mm and a theoretical drug loading identical to the layered rod.

Evaluation of Drug Release:

Sulindac and clonidine HCl loaded rods were incubated in 10 mL of phosphate buffered saline (Hyclone 0.0067M) at 37° C. under mild agitation. At pre-selected times, the buffer was removed for analysis and replaced with new medium. The drug content of the release samples was assayed using a Perkin Elmer Lambda 850 ultraviolet/visible (UV/VIS)

spectrophotometer. Sulindac was quantified at 328 nm and clonidine HCl was quantified at 226 nm.

Figure 5:
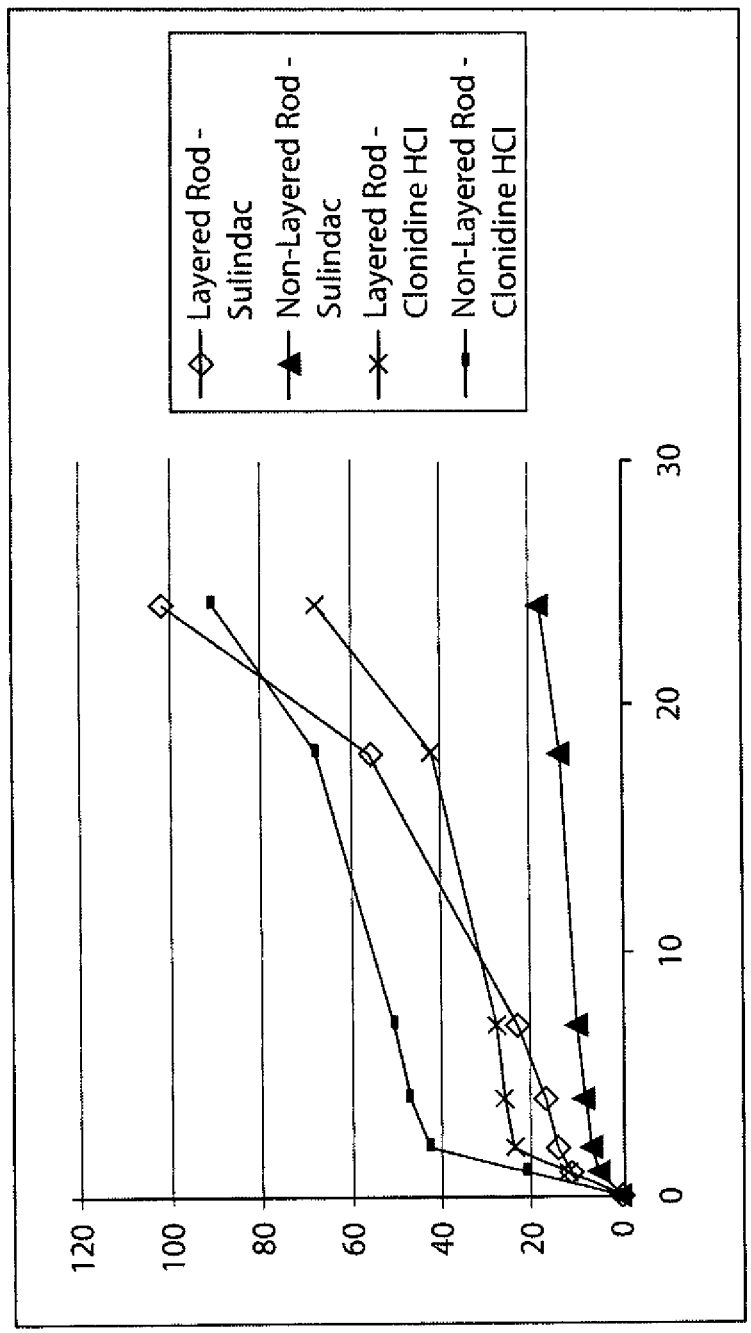
FIG. 5 is a graph illustrating the in vitro cumulative release (y-axis; %) of sulindac and clonidine HCl over time (x-axis; days) from implantable layered and non-layered medical devices prepared using a PLGA 50:50 polymer as described in Example 3.

FIG. 5 is a graph showing the cumulative release of sulindac (%) and clonidine HCl (%) from the PLGA 50:50 over the given time period in days. The graph shows the increased sulindac elution rate with the layered rod approach compared to the non-layered version. Furthermore, the clonidine HCl elution rate was similar for both rod configurations. However, there was a higher initial clonidine HCl burst in the non-layered rod compared to the layered rod.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A medical device comprising:
    a non-tubular first section comprising a first polymer absent of a biologically active agent, the first polymer being biodegradable;
    a non-tubular second section fused to the first section by heating the first polymer above its glass transition temperature, wherein the second section comprises a second polymer having at least one biologically active agent comprising clonidine hydrochloride disposed therein comprising 10 wt % of the second section, the at least one biologically active agent having a particle size of 5 micrometers to 150 micrometers and the second polymer being biodegradable and having an ester end capped polymer chain,
    wherein the device is an orthopedic implant and is adapted to release the first biologically active agent for greater than 1 day when implanted in a subject and the medical device is biodegradable, and
    wherein at least one of the sections is porous and comprises at least 50% void volume, the first polymer comprises poly(glycolide-co-caprolactone), and the second polymer comprises poly(lactic-co-glycolic acid) (PLGA) having an intrinsic viscosity (IV) of 0.57.

2. The medical device of claim 1 further comprising a third section attached to the second section, wherein the third section comprises a third polymer comprising poly(glycolide-co-caprolactone absent of a biologically active agent.

3. A medical device comprising:
    a first section comprising a first polymer absent of a biologically active agent, the first polymer being biodegradable;
    a non-tubular second section fused to the first section by heating the first polymer above its glass transition temperature, wherein the second section comprises a second polymer having at least a first biologically active agent comprising clonidine hydrochloride disposed therein comprising 10 wt % of the second section, the first biologically active agent having a particle size of 5 micrometers to 150 micrometers, and the second polymer being biodegradable and having an ester end capped polymer chain; and
    a third section fused to the second section, wherein the third section comprises a third polymer absent of a biologically active agent, the third polymer being biodegradable;
    wherein the device is an orthopedic implant and is adapted to release the first biologically active agent for greater than 1 day when implanted in a subject and the medical device is biodegradable, and
    wherein at least one of the sections is porous and comprises at least 50% void volume, the first polymer and the third polymer comprises poly(glycolide-co-caprolactone), and the second polymer comprises poly(lactic-co-glycolic acid) (PLGA) having an intrinsic viscosity (IV) of 0.57.

4. The medical device of claim 3 wherein the device has an exposed surface comprising a portion of the surface of the non-tubular second section.

5. The medical device of claim 3 wherein at least two of the polymers differ by one or more characteristics selected from the group consisting of chemical structure, morphology, molecular weight, hydrophilicity, hydrophobicity, porosity, biodegradability, degradation rate, tacticity, toughness, and mechanical properties.

6. The medical device of claim 3 wherein the device is adapted to release the first biologically active agent for greater than 20 days when implanted in a subject.

7. The medical device of claim 3 wherein the second section is configured to provide an initial burst of the first biologically active agent.

8. The medical device of claim 3 wherein the clonidine hydrochloride has a drug load of 3600 micrograms.

9. The medical device of claim 3 wherein the second polymer is stabilized with butylated hydroxytoluene (BHT).

10. A substantially cylindrically-shaped medical device comprising:
    a first disc comprising a first polymer absent of a biologically active agent, the first polymer being biodegradable;
    a second disc having a first face fused to a face of the first disc by heating the first polymer above its glass transition temperature, wherein the second disc comprises a second polymer having at least one biologically active agent comprising clonidine hydrochloride disposed therein comprising 10 wt % of the second disc, the at least one biologically active agent having a particle size of 5 micrometers to 150 micrometers, and the second polymer being biodegradable and having an ester end capped polymer chain; and
    a third disc fused to a second face of the second polymer, wherein the third disc comprises a third polymer absent of a biologically active agent, the third polymer being biodegradable;
    wherein the device is an orthopedic implant and is adapted to release the first biologically active agent for greater than 1 day when implanted in a subject and the medical device is biodegradable, and
    wherein at least one of the discs is porous and comprises at least 50% void volume, the first polymer and the third polymer comprises poly(glycolide-co-caprolactone), and the second polymer comprises poly(lactic-co-glycolic acid) (PLGA) having an intrinsic viscosity (IV) of 0.57.

11. The medical device of claim 10 wherein the device is adapted to release the first biologically active agent for greater than 20 days when implanted in a subject.

* * * * *